US011844641B2

(12) United States Patent
Fuller

(10) Patent No.: US 11,844,641 B2
(45) Date of Patent: Dec. 19, 2023

(54) METHOD AND DEVICE FOR PRODUCING AND USING MULTIPLE ORIGINS OF X-RADIATION

(71) Applicant: Michael Keith Fuller, Salinas, CA (US)

(72) Inventor: Michael Keith Fuller, Salinas, CA (US)

( * ) Notice: Subject to any disclaimer, the term of this patent is extended or adjusted under 35 U.S.C. 154(b) by 5 days.

(21) Appl. No.: 17/300,467

(22) Filed: Jul. 12, 2021

(65) Prior Publication Data

US 2022/0328277 A1    Oct. 13, 2022

Related U.S. Application Data

(60) Provisional application No. 63/048,276, filed on Jul. 6, 2020.

(51) Int. Cl.
*H01J 35/10* (2006.01)
*H01J 35/26* (2006.01)
(Continued)

(52) U.S. Cl.
CPC ............ *A61B 6/484* (2013.01); *A61B 6/4021* (2013.01); *H01J 35/10* (2013.01); *H01J 35/26* (2013.01); *H01J 35/28* (2013.01); *H01J 35/305* (2013.01); *H05G 1/52* (2013.01); *A61B 6/5205* (2013.01); *G01N 23/041* (2018.02); *G21K 2207/005* (2013.01); *H01J 2235/068* (2013.01); *H01J 2235/081* (2013.01); *H01J 2235/086* (2013.01)

(58) Field of Classification Search
None
See application file for complete search history.

(56) References Cited

U.S. PATENT DOCUMENTS 6,583,420 B1 *  6/2003  Nelson ................. A61B 6/4258
                                                         250/397
6,693,291 B2 *  2/2004  Nelson ................. A61B 6/4028
                                                         250/363.01

(Continued)

FOREIGN PATENT DOCUMENTS

| DE | 102005062447 A1 * | 7/2007 | ............... A61B 6/00 |
| EP | 1803398 B1 * | 7/2010 | ............... A61B 6/00 |
| WO | WO-2010150136 A1 * | 12/2010 | ............. A61B 6/032 |

*Primary Examiner* — Thomas R Artman

(57) ABSTRACT

An x-ray tube source is disclosed that allows differential phase shift, attenuation, and x-ray scattering features of an object to be acquired in a single exposure. Such multiplexed x-ray tube source includes multiple x-ray spot origins controlled in such a way that each slightly separated spot is temporally modulated "ON and OFF" at differing frequencies. In an x-ray interferometer system, such x-ray tube source forms multiple illumination beams of a single angular view of an object's feature but each with different interference fringe locations. A composite image can be acquired with a high frame-rate digital detector as a component element in such x-ray interferometer system. Such composite image can be subsequently de-multipexed and separately presented according to each spot-source illumination beam. Such isolated images of an object's feature, each having different fringe locations, allows for post-acquisition "fringe-mapping" analysis of the feature's full interaction with x-rays, including refraction, scattering, and absorption.

9 Claims, 3 Drawing Sheets

(51) Int. Cl.
*H01J 35/28* (2006.01)
*H01J 35/30* (2006.01)
*H05G 1/52* (2006.01)
*A61B 6/00* (2006.01)
*G01N 23/041* (2018.01)

(56) References Cited

U.S. PATENT DOCUMENTS

| | | | | |
|---|---|---|---|---|
| 7,042,975 | B2* | 5/2006 | Heuscher | A61B 6/027 378/15 |
| 7,147,372 | B2* | 12/2006 | Nelson | A61B 6/4233 378/207 |
| 7,305,063 | B2* | 12/2007 | Heuscher | H01J 35/147 378/151 |
| 7,817,777 | B2* | 10/2010 | Baumann | A61B 6/00 378/62 |
| 8,009,796 | B2* | 8/2011 | Popescu | A61B 6/032 378/19 |
| 8,259,905 | B2* | 9/2012 | Al-Sadah | H01J 35/26 378/126 |
| 8,619,946 | B2* | 12/2013 | Hanke | H01J 35/153 378/124 |
| 9,237,872 | B2* | 1/2016 | Tkaczyk | A61B 6/502 |
| 9,412,481 | B1* | 8/2016 | Fuller | G01N 23/201 |
| 9,870,892 | B2* | 1/2018 | Behling | H01J 35/10 |
| 9,939,392 | B2* | 4/2018 | Wen | G01N 23/041 |
| 10,269,528 | B2* | 4/2019 | Yun | H01J 35/10 |
| 11,123,027 | B2* | 9/2021 | Schwoebel | H01J 35/10 |
| 11,152,130 | B2* | 10/2021 | Akinwande | H01J 35/186 |
| 11,534,118 | B2* | 12/2022 | Schwoebel | A61B 6/06 |
| 2003/0205676 | A1* | 11/2003 | Nelson | A61B 6/4258 250/370.09 |
| 2003/0209672 | A1* | 11/2003 | Nelson | A61B 6/4258 250/505.1 |
| 2004/0008810 | A1* | 1/2004 | Nelson | A61B 6/4488 378/19 |
| 2004/0081270 | A1* | 4/2004 | Heuscher | A61B 6/027 378/4 |
| 2005/0100126 | A1* | 5/2005 | Mistretta | A61B 6/032 378/15 |
| 2006/0182223 | A1* | 8/2006 | Heuscher | H01J 35/30 378/137 |
| 2007/0153979 | A1* | 7/2007 | Baumann | A61B 6/4021 378/138 |
| 2009/0154640 | A1* | 6/2009 | Baumann | A61B 6/484 378/19 |
| 2010/0074392 | A1* | 3/2010 | Behling | H01J 35/153 378/124 |
| 2010/0080341 | A1* | 4/2010 | Popescu | A61B 6/4291 378/19 |
| 2010/0290595 | A1* | 11/2010 | Al-Sadah | H01J 35/28 378/138 |
| 2011/0122992 | A1* | 5/2011 | Hanke | H01J 35/153 378/124 |
| 2014/0205073 | A1* | 7/2014 | Tkaczyk | A61B 6/4021 378/126 |
| 2014/0307853 | A1* | 10/2014 | Behling | H01J 35/10 378/62 |
| 2016/0351370 | A1* | 12/2016 | Yun | H01J 35/10 |
| 2019/0206652 | A1* | 7/2019 | Akinwande | G01N 23/041 |
| 2020/0305809 | A1* | 10/2020 | Schwoebel | H01J 35/147 |
| 2021/0338181 | A1* | 11/2021 | Schwoebel | A61B 6/4021 |
| 2022/0328277 | A1* | 10/2022 | Fuller | H01J 35/064 |

* cited by examiner

METHOD AND DEVICE FOR PRODUCING AND USING MULTIPLE ORIGINS OF X-RADIATION

A method and device is disclosed for the generation and use of multiple localized origins of x-rays, particularly for imaging the internal features of objects.

FIELD

The present invention relates to the generation of high-intensity hard x-rays in localized origins, useful for obtaining images using phase-shifted and scattered x-rays.

BACKGROUND

Compared to traditional x-ray absorption radiography, phase radiography is better suited for visualizing soft-tissue structures which do not appreciably absorb x-rays, but which may contain non-absorptive structural details. Internal structures may produce a measurable deviation in the direction and velocity of the incident radiation because of local variations in the refractive index, and variations in density and thickness of those structures. Phase disturbances occur at interfaces between soft-tissue planes that have slightly different refractive indices and thicknesses. Within soft-tissues, incident radiation is refracted by spatially oriented molecular and atomic planes, thereby experiencing a significant shift in phase, corresponding to a change in direction.

For hard x-rays, the cross section for absorption, which generates the contrast in conventional radiography, is usually much smaller than that for elastic scattering. The elastic scattering causes a phase shift of the wave passing through matter. Thus, the possibility to record the elastic scattering and phase shift of x-rays opens the potential for greatly enhanced contrast and, in consequence, reduction of the applied x-ray dose. Reduction of the dose is desirable i) because of health risks for patients exposed to x-rays, and ii) because of the reduced exposure times.

Several methods to detect phase variations in the radiation behind the sample were developed in the past years. They can be classified into interferometric methods, techniques using an analyzer crystal, and free-space propagation methods. These methods differ in the nature of the signal recorded, the experimental setup, and the requirements on the illuminating radiation (especially its spatial coherence and monochromaticity). Many experimental results known in the prior art were obtained at synchrotron x-ray sources, which are highly expensive installations and are only available at distinct scientific facilities. The commercial impact of an invention in context with radiography will greatly depend on whether an x-ray tube is suitable as radiation source or whether the method is restricted to use at synchrotron radiation facilities because of the required degree of coherence.

The use of gratings as optical elements in hard x-ray phase imaging has shown the potential of overcoming the problems that so far impair the wider use of phase contrast in x-radiography and tomography. Several different geometries of grating-based interferometers for hard x-rays have been investigated recently.

The Talbot-Lau self-imaging effect, i.e., its replication in the longitudinal direction without the use of a lens, has been widely studied and used for a number of applications, including x-ray phase imaging and x-ray dark-field scatter imaging. Talbot self-imaging can be described in the following way: a (quasi-) monochromatic wavefield of wavelength $\lambda$ with lateral period $1/v_1$ is also longitudinally periodic. The longitudinal period $z_T$—often referred to as the Talbot-distance—is given as $z_T = 2/\lambda v_1^2$. A common practical implementation of the Talbot effect is achieved when one 1D grating is illuminated by x-rays proceeding from a monochromatic spatially coherent point source and the grating pattern is replicated at certain far-field distances.

The Lau effect is the spatially incoherent counterpart of the Talbot effect. The Lau effect is obtained when one allows the superposition in consonance of Talbot fringes generated by a series of mutually incoherent quasi-monochromatic sources. A common practical implementation of the Lau effect is achieved when two 1D gratings, oriented parallel to each other, are illuminated by the x-rays proceeding from a quasi-monochromatic spatially incoherent planar source, and the grating pattern is replicated at certain far-field distances.

The second grating divides the incoming beam essentially into the two first diffraction orders. The angle between the two diffracted beams is so small that they overlap almost completely. In the overlap region downstream of the second grating, the diffracted beams interfere and form linear periodic fringe patterns in planes perpendicular to the optical axis, at a Talbot distance down-stream of the second grating.

The period of the x-ray interference pattern is usually in the range of a few microns, which can only be conveniently resolved by a very high resolution detector in combination with a very intense illumination and hence, limits the field-of-view significantly. For this reason, an analyzer grating, typically an absorption grating, is placed at a fractional Talbot length to analyze the interference pattern. The analyzer grating, normally having the same period as the self-imaged interference fringes, can be scanned in the transverse direction in a technique called "phase-stepping." An alternative approach is the retrieval of the differential phase by using Moiré fringes when inclining the analyzer grating against the source gratings. A further alternative replaces the mechanical scanning of the analyzer grating with a "swept" electron column within the x-ray tube. A variation of this alternative can be used with the Moiré fringe technique (See Proc Natl Acad Sci USA. 2014 Dec. 30; 111 (52): 18799). U.S. Pat. No. 9,939,392 discloses utilization of this alternative approach. In any of these prior art methods, multiple exposures—separate images acquired with the x-ray origin and/or gratings in slightly different physical positions—are required.

Multiple exposures can introduce motion artifacts and other errors into the image. The problem also occurs in Computed Tomography (CT) scans, where a single point x-ray source is rotated around the sample as series of "time and angle" images are acquired. A solution for CT has been demonstrated by multiplexing multiple sources (see: August 2006 Applied Physics Letters 89(6):064106-064106-3). In that prior work, the array of nanotube field-emitter cathode equipped x-ray tubes each flash on and off at different rates. A single fast frame-rate detector acquires multiple images simultaneously. The complex image is then de-multiplexed to separate its component angular images, post-acquisition. The component images can then be used to construct a 3-D map image of the sample. Generally, field-emitter cathodes cannot produce high current electron beams compared to thermotic cathodes. Additionally, separate x-ray tubes are not suitable for application requiring close coupling of multiple x-ray sources.

U.S. Pat. No. 9,412,481 discloses a similar method using a large array of Fresnel biprisms. That technique tends to effectively enlarge the x-ray origin, thus reducing image resolution, albeit somewhat mitigated by the use of curved arrays.

X-ray origin size tends to be limited by the ability of the anode to dissipate the heat that is associated with the impact of the electron column emitted from the cathode. This phenomenon is sometimes described as instantaneous heat buildup and residual heat buildup. A standard approach to meet the challenge is to set the size of the impact region to deal with instantaneous heat buildup and to rotate the anode to deal with residual heat buildup. Typically, the impact zone is elongated relative to the view port of the x-ray tube and the anode is formed as a metal layer on a rapidly rotating disk. Despite these accommodations, many rotating anode x-ray tubes cannot use very small origins and often fail when the "track" on the anode disk melts under the heat load.

X-ray produced from such x-ray tubes are not efficiently used in grating-based interferometry setups for phase and dark-field radiography. Additionally, large-format x-ray gratings with high aspect ratios and small periods are difficult to fabricate. Moreover, multiple exposures, required in both mechanical phase stepping and swept-electron column phase stepping, can introduce motion artifacts and other errors into the image.

Cylindrical metal anode x-ray tubes are commercially available. Rigaku provided a simple periodically patterned version of one of these products. Previously, rotating and slewing cylindrical metal anode x-ray tubes have been proposed but seemingly never built. Rotating and slewing cylindrical metal anode x-ray tubes have not been proposed or built that achieve multiple spot origins through electron focusing. Similarly, rotating and slewing cylindrical metal anode x-ray tubes have not been proposed or built that use complex patterning to achieve multiplexing in x-ray spots. Additionally, rotating disk metal anode x-ray tubes have not been proposed or built that use complex patterning to achieve multiplexing in x-ray spots through swept electron beamlets.

An alternative method in needed to produce multiple high-intensity localized origins of x-rays. A need also exists for an alternative method that would allow simultaneous acquisition of phase contrast and dark-field images without the need for phase stepping. Lastly, a need exists for a longer-lifetime laboratory x-ray tube source.

SUMMARY OF THE INVENTION

It is the object of the present invention to provide a method and apparatus for multiple x-ray origins from a rotating anode x-ray tube, useful for obtaining images using phase-shifted and scattered x-rays.

This objective is achieved in the present invention by devices, comprising:
 a) an x-ray source, preferably a rotating and/or slewing cylindrical anode combined with a cathode, that produces multiple small columns of pulsed electrons.
 b) an x-ray source, preferably a rotating and slewing cylindrical anode combined with a cathode, that produces several columns of electrons, whereby each column impacts alternately an x-ray producing metal or a non-x-ray producing material, during the slew cycle.
 c) an x-ray source, preferably a rotating disk anode combined with a cathode, that produces several swept columns of electrons, whereby each column impacts alternately an x-ray producing metal or a non-x-ray producing material, during the sweep cycle.

BRIEF DESCRIPTION OF THE SEVERAL VIEWS OF THE DRAWING

The invention will be further described, by way of example only, with reference to the accompanying drawings, in which.

DETAILED DESCRIPTIONS OF THE DRAWINGS

Figure 1:
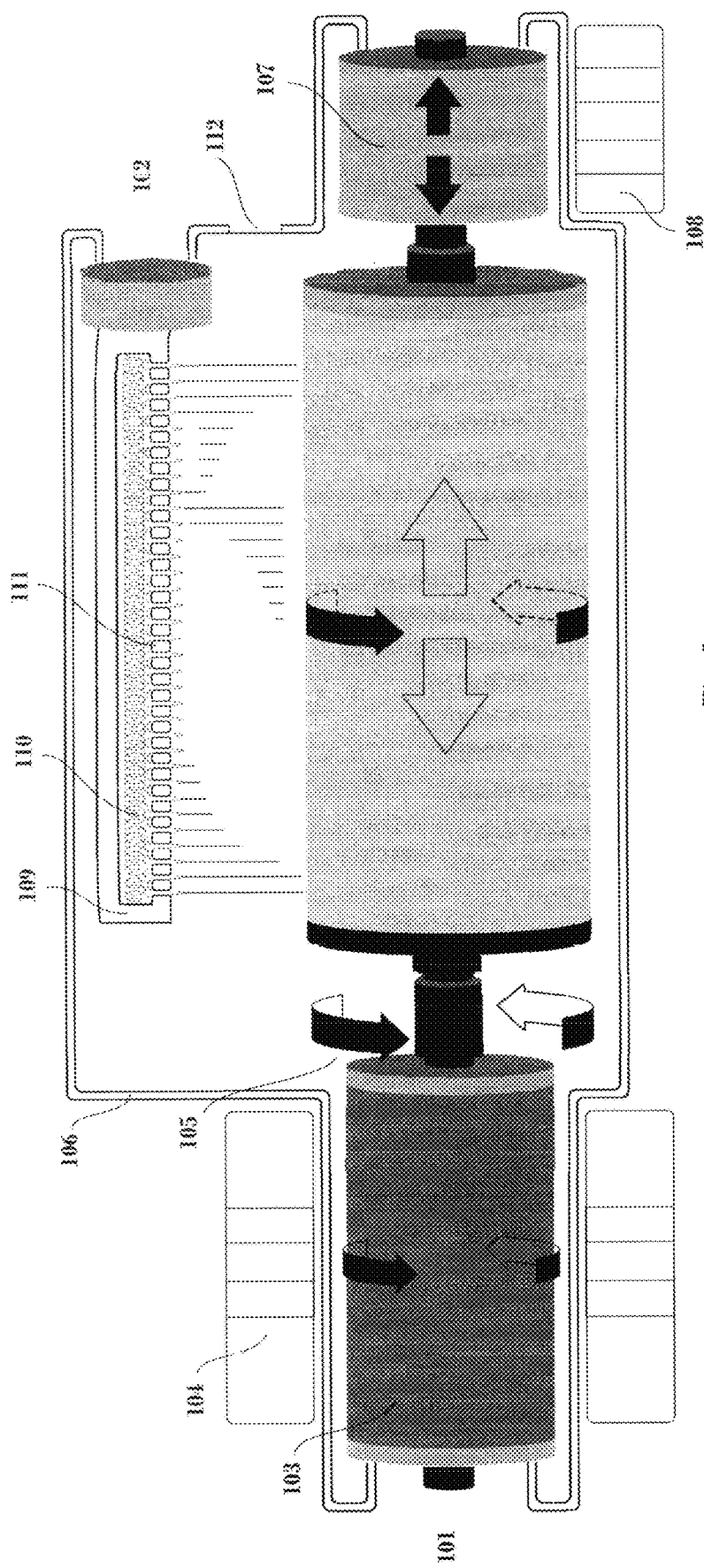
FIG. 1 is a diagrammatic view of a rotating anode x-ray tube consisting of a metal-coated cylinder attached to a rotational driving motor and a linear actuator, and presented opposite an array of individually-pulsed electron sources.

In a preferred embodiment of the present invention a rotating anode consists of a driven metal-coated cylinder attached to a driving motor (FIG. 1). Alternatively, a fixed anode or a rotating anode consisting of a metal-coated disk can be used, albeit with reduced capability for heat dissipation. The assembly of FIG. 1 is comprised of a vacuum envelope of metal and glass or ceramic, to stand off the high voltage between the anode 101 and the cathode 102. Typically, the rotor 103 is inside the envelope and the stator 104 is outside the envelope. A slip coupling 105 provides rotational power transfer while allowing longitudinal movement of the cylinder. The envelope walls 106 provide sufficient resistance to reactive forces. Longitudinal slewing of the cylinder is provided by a linear actuator 107 and actuator controller 108.

High speed rotation (e.g. 7000 RPM) allows for dissipation of residual heat from the array of fine focusing electron emitters 109. The array consists of a source of electrons 110 and electron gating and focusing optics 111. Further heat dissipation is allowed by modest adjustment of the linear actuator 107, such that multiple helical paths are traversed on the surface of the metal cylinder. The pulsed electron columns impact regions on the metal cylinder do not change position relative to the view port 112 of the tube assembly. The linear actuator will reverse direction automatically, providing another helical path albeit in opposite twist direction, hence more surface of the metal cylinder is used to dissipate heat buildup.

Figure 2:
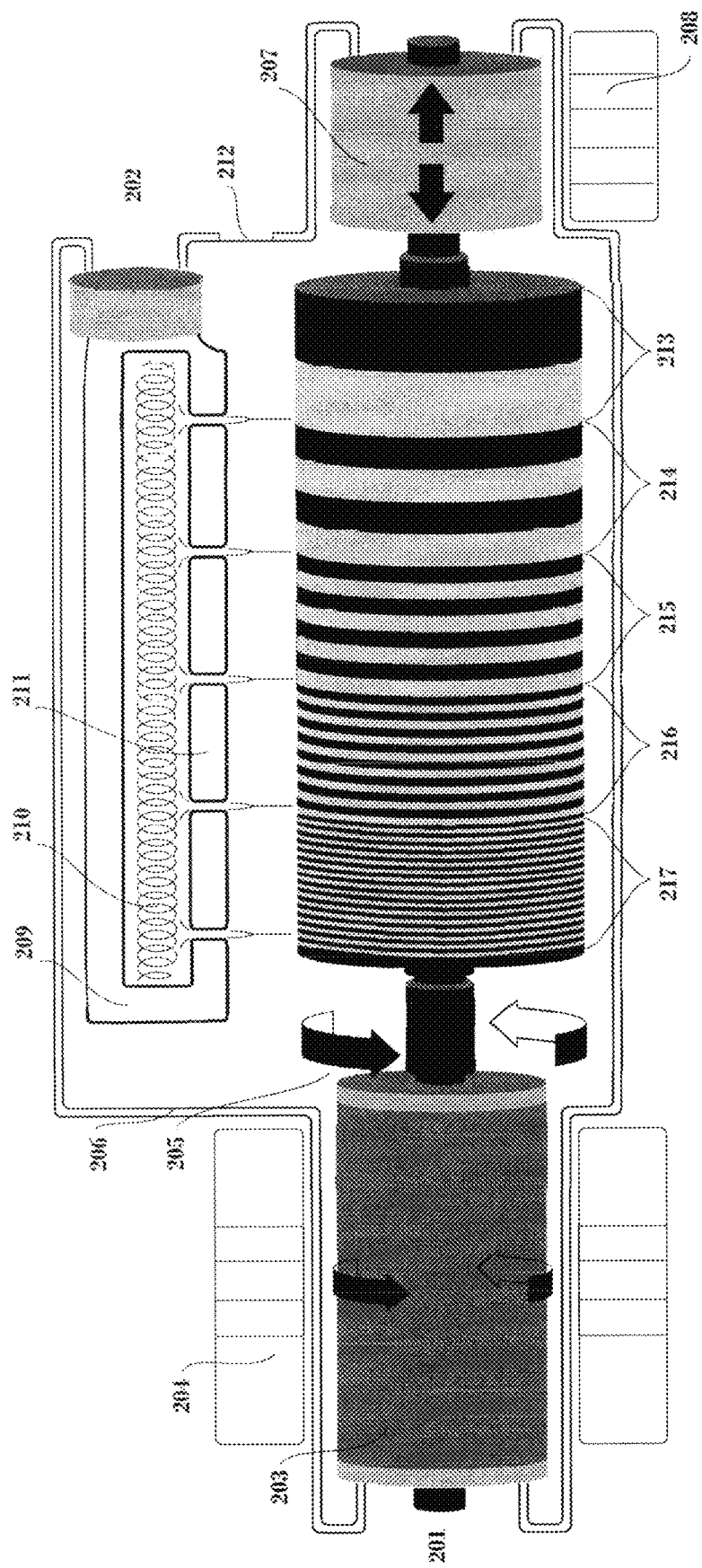
FIG. 2 is a diagrammatic view of a rotating anode x-ray tube consisting of a patterned metal-coated cylinder attached to a rotational driving motor and a linear actuator, and presented opposite an array of continuous electron sources.

In another preferred embodiment of the present invention a rotating anode consists of a driven metal-coated cylinder attached to a driving motor (FIG. 2). The assembly is comprised of a vacuum envelope of metal and glass or ceramic, to stand off the high voltage between the anode 201 and the cathode 202. Typically, the rotor 203 is inside the envelope and the stator 204 is outside the envelope. A slip coupling 205 provides rotational power transfer while allowing longitudinal movement of the cylinder. The envelope walls 206 provide sufficient resistance to reactive forces. Longitudinal slewing of the cylinder is provided by a linear actuator 207 and actuator controller 208.

High speed rotation (e.g. 7000 RPM) allows for dissipation of residual heat from the array of course focusing electron emitters 209. The array consists of a source of electrons 210 and electron focusing optics 211. Further heat dissipation is allowed by modest adjustment of the linear actuator 207, such that multiple helical paths are traversed on the surface of the metal cylinder. The electron columns impact regions on the metal cylinder do not change position relative to the view port 212 of the tube assembly. The linear actuator 207 will reverse direction automatically, providing another helical path albeit in opposite twist direction, hence more surface of the metal cylinder is used to dissipate heat buildup. More significantly, linear actuation changes the alignment of the electron beams with metal sections of the anode. This allows on/off cycling of each electron column, and hence, the pulsing of the associated x-ray spot. One complete cycle of the linear actuator may take one half second.

The cylinder anode is partially coated in metal, which produce hard x-rays, and partially uncoated or covered in electrically insulating material, which prevent the generation of hard x-rays. Specifically, adjacent longitudinal regions of identical length on the anode are metal coated in simple patterns, each with different frequencies of the coating pattern.

One complete cycle of the linear actuator will be precisely the distance of one longitudinal region of the partially coated anode. The linear actuator will reverse direction automatically, providing electrical continuity, followed by discontinuity, in the vacuum gap between the cathode and cylindrical anode. The result, as the anode metallic sections alternatively align and/or misalign with the emitters of the electron beams, is multiple x-ray spots from the same tube that flash on and off at different rates (e.g. 2 Hz for one spot, 4 Hz for the next spot, 8 Hz, for the next spot, 16 Hz for the next spot, 32 Hz for the next spot, etc.).

Figure 3:
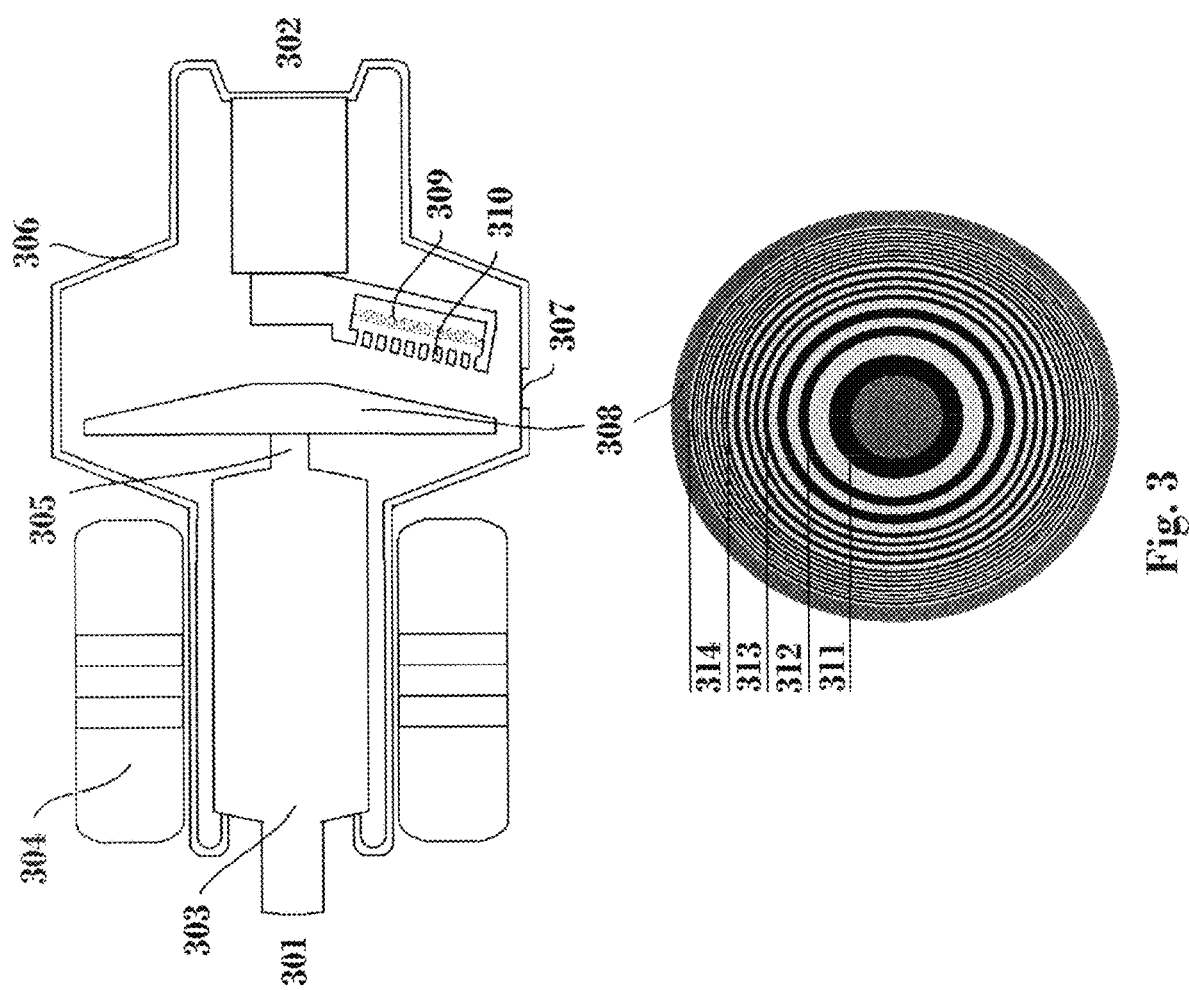
FIG. 3 is a diagrammatic view of a rotating anode x-ray tube consisting of a motor-driven metal-coated disk, and presented opposite an array of continuous electron sources controlled by electron focusing and sweeping optics.

In another preferred embodiment of the present invention a rotating anode consists of a driven metal-coated disk attached to a driving motor (FIG. 3). The assembly is comprised of a vacuum envelope of metal and glass or ceramic, to stand off the high voltage between the anode 301 and the cathode 302. Typically, the rotor 303 is inside the envelope and the stator 304 is outside the envelope. An anode stem 305 provides rotational power transfer. The envelope walls 306 provide sufficient resistance to reactive forces. A view port provides almost unimpeded transmission of x-rays 307.

The anode 308 is shown in side and face views in FIG. 3. High speed rotation (e.g. 7000 RPM) allows for dissipation of residual heat from the array of course focusing electron emitters, consisting of a source of electrons 309 and electron focusing and steering optics 310.

The steering of the electron columns proceeds in radially, in respect to the anode disk, and will reverse direction automatically. One complete cycle of the electron sweeping action may take one half second.

The disk anode is partially coated in metal, which produce hard x-rays, and partially uncoated or covered in electrically insulating material, which prevent the generation of hard x-rays. Specifically, adjacent concentric regions of identical radial length on the disk anode are metal coated in simple patterns, each with different frequencies of the coating pattern.

One complete cycle of the swept electron beamlets will be precisely the distance of one radial distance region of the partially coated anode. The sweeping action will reverse direction automatically, providing electrical continuity, followed by discontinuity, in the vacuum gap between the cathode and cylindrical anode. The result is multiple x-ray spots from the same tube that flash on and off at different rates (e.g. 2 Hz for one spot, 4 Hz for the next spot, 8 Hz, for the next spot, 16 Hz for the next spot, 32 Hz for the next spot, etc.).

DETAILED DESCRIPTION OF THE INVENTION

The present invention overcomes the drawbacks of the prior art by allowing scattering and phase-contrast images to be obtained with a single exposure. A typical multiple exposure method requires the repositioning of an analyzer grating, or alternatively, the repositioning of the origin spot within the x-ray tube. This allows "fringe mapping" across a feature within a sample and at least six separate images are required. This invention allows all six images to be acquired simultaneously and separated in post-acquisition processing, followed by image analysis to derive the phase and/or scattering images. This invention allows all needed images to be acquired simultaneously and separated in post-acquisition processing, followed by image analysis to derive the phase and/or scattering images.

This invention accomplished this by use of multiplexing x-ray phase radiography using a multiplexed x-ray tube source which can generate spatially and temporally modulated radiation for parallel imaging processing. Demultiplexing of the composite image recovers the original separate channels from the multiplexed signal. This allows for an increase in imaging speed and reduction of object motion artifacts and setup motion artifacts in the resulting x-ray phase images.

What is claimed is:

1. An x-ray tube device, comprising: a vacuum chamber, an anode, and a cathode comprised of an array of electron emitters, wherein said x-ray tube device produces spatially distributed x-ray origins configured to generate x-ray beams at different illuminating angles relative to an interferometer, wherein individual x-ray origins pulse on-and-off at different frequencies, wherein the duty cycles of said pulsing for each of said individual x-ray origins partially overlap.

2. The x-ray tube device of claim 1, wherein the anode is a rotating disk anode.

3. The x-ray tube device of claim 1, wherein the anode is a rotating cylinder anode.

4. The x-ray tube device of claim 3, wherein the rotating cylinder anode is simultaneously linearly translated, wherein said linear translation is oscillating.

5. The x-ray tube device of claim 1, wherein said varied frequencies are determined by operation of said electron emitters.

6. An x-ray tube device, comprising: a vacuum envelope, an anode, and an array of electron emitters, wherein the electron emitters operate continuously, wherein said x-ray tube device produces spatially distributed x-ray origins configured to generate x-ray beams at different illuminating angles relative to an interferometer, where said anode is a rotating cylinder comprised of a first region that generates x-rays when impinged upon by electrons, wherein the first region is arrayed in a discrete pattern of stepped spatial frequencies, and where the anode has a second region that does not generate detectable x-rays, wherein said discrete pattern is arranged parallel to said axis of target rotation such that oscillatory translation of the anode alternately aligns each of the continuous electron emissions with the first region or the second region, wherein individual x-ray origins pulse on-and-off at different frequencies, wherein the duty cycles of said pulsing for each of said individual x-ray origins partially overlap.

7. An x-ray tube device, comprising: a vacuum envelope, an anode, and an array of electron emitters, wherein the electron emitters operate continuously wherein said x-ray tube device produces spatially distributed x-ray origins configured to generate x-ray beams at different illuminating angles relative to an interferometer, where said anode is comprised of a first region that generates x-rays when impinged upon by electrons, wherein the first region is arrayed in a discrete pattern of stepped spatial frequencies, and where the anode has a second region that does not generate detectable x-rays, wherein that oscillatory sweeping of the electron beams alternately aligns each of the continuous electron emissions with the first region or the second region, wherein individual x-ray origins pulse on-and-off at different frequencies, wherein the duty cycles of said pulsing for each of said individual x-ray origins partially overlap.

8. The x-ray tube device of claim 7, wherein the anode is a rotating disk anode.

9. The x-ray tube device of claim 7, wherein the anode is a rotating cylinder anode.

* * * * *